United States Patent
Yamane

(10) Patent No.: US 11,722,643 B2
(45) Date of Patent: Aug. 8, 2023

(54) MEDICAL-USE CONTROL SYSTEM, IMAGE PROCESSING SERVER, IMAGE CONVERTING APPARATUS, AND CONTROL METHOD

(71) Applicant: Sony Group Corporation, Tokyo (JP)

(72) Inventor: Masahito Yamane, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 17/910,368

(22) PCT Filed: Mar. 18, 2021

(86) PCT No.: PCT/JP2021/010989
§ 371 (c)(1),
(2) Date: Sep. 9, 2022

(87) PCT Pub. No.: WO2021/200193
PCT Pub. Date: Oct. 7, 2021

(65) Prior Publication Data
US 2023/0128027 A1    Apr. 27, 2023

(30) Foreign Application Priority Data
Mar. 31, 2020   (JP) ................................ 2020-062191

(51) Int. Cl.
*H04N 7/18*   (2006.01)
*H04N 5/268*   (2006.01)
(Continued)

(52) U.S. Cl.
CPC ............. *H04N 7/181* (2013.01); *A61B 90/37* (2016.02); *H04N 5/268* (2013.01); *H04N 7/0127* (2013.01); *H04L 67/12* (2013.01)

(58) Field of Classification Search
CPC ........ H04N 7/181; H04N 7/0127; H04N 7/18; H04N 7/01; H04N 5/268; H04L 67/12; A61B 90/37
(Continued)

(56) References Cited

U.S. PATENT DOCUMENTS

| 8,312,133 B2 * | 11/2012 | Kurosawa | .......... H04N 21/2402 |
| | | | 709/224 |
| 9,135,274 B2 * | 9/2015 | Rachev | .................. G16H 40/67 |

FOREIGN PATENT DOCUMENTS

| JP | 2005-57590 A | 3/2005 |
| JP | 2013-518495 A | 5/2013 |

(Continued)

OTHER PUBLICATIONS

International Search Report and Written Opinion dated Jun. 15, 2021, received for PCT Application PCT/JP2021/010989, filed on Mar. 18, 2021, 12 pages including English Translation.
(Continued)

*Primary Examiner* — Sherrie Hsia
(74) *Attorney, Agent, or Firm* — Xsensus LLP

(57) ABSTRACT

A sending-side image converting apparatus sends a transmission image to a network. An image processing server performs image processing on the transmission image and sends the image generated by the image processing to the network. A receiving-side image converting apparatus outputs display images converted from the transmission image and the image generated by the image processing, to a display apparatus. Further, a controlled delay time based on a difference between a delay time in a first transmission path without via the image processing server and a delay time in a second transmission path via the image processing server is obtained on the basis of a characteristic of the display apparatus, and a timing at which the images are output to the display apparatus is controlled. The present technology is
(Continued)

applicable to, for example, a medical-use image transmission system.

14 Claims, 11 Drawing Sheets

(51) Int. Cl.
  *A61B 90/00* (2016.01)
  *H04N 7/01* (2006.01)
  *H04L 67/12* (2022.01)
(58) Field of Classification Search
  USPC .......................................................... 348/143
  See application file for complete search history.

(56) References Cited

FOREIGN PATENT DOCUMENTS

| JP | 2019-162231 A | 9/2019 |
| WO | 2012/081170 A1 | 6/2012 |
| WO | 2018/088026 A1 | 5/2018 |
| WO | 2019/123874 A1 | 6/2019 |
| WO | 2019/176556 A1 | 9/2019 |

OTHER PUBLICATIONS

Nishikawa, "Is your TV lagging? What you need to know about delays", Zenji Nishikawa's Big Screen, Available Online At: https://av.watch.impress.co.jp/docs/series/dg/1236788.html, Mar. 5, 2020, pp. 1-16 (34 pages including English Translation).

* cited by examiner

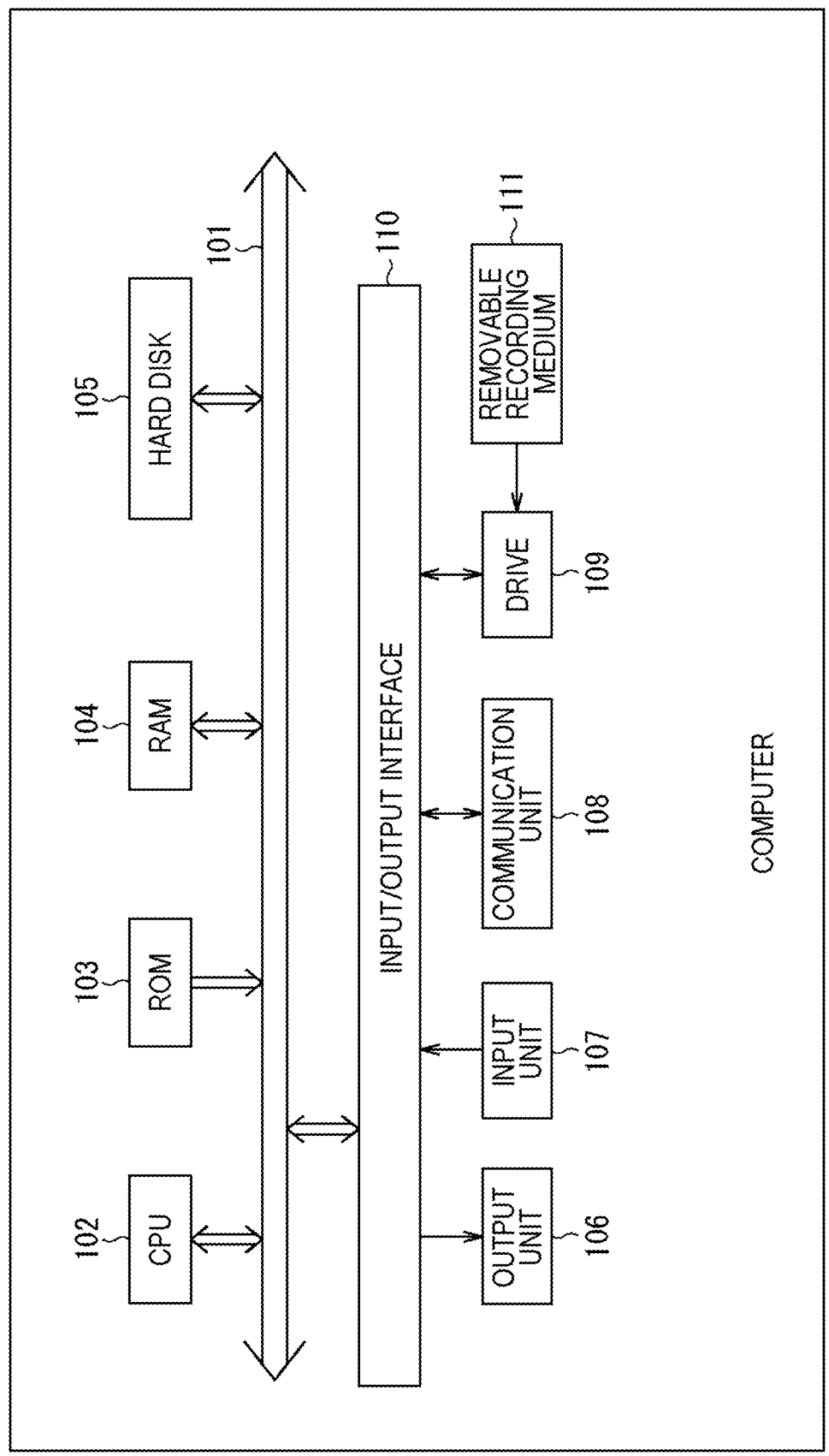

MEDICAL-USE CONTROL SYSTEM, IMAGE PROCESSING SERVER, IMAGE CONVERTING APPARATUS, AND CONTROL METHOD

CROSS-REFERENCE TO RELATED APPLICATIONS

The present application is based on PCT filing PCT/JP2021/010989, filed Mar. 18, 2021, which claims priority to JP 2020-062191, filed Mar. 31, 2020, the entire contents of each are incorporated herein by reference.

TECHNICAL FIELD

The present disclosure relates to a medical-use control system, an image processing server, an image converting apparatus, and a control method, and particularly relates to a medical-use control system, an image processing server, an image converting apparatus, and a control method that are devised to enable reduction of a period in which medical information and the like are not displayed in switching an image transmission path.

BACKGROUND ART

In recent years, a system has been proposed, in which various medical devices are connected in a network manner, and multiple pieces of information of the plurality of medical devices are integrated and displayed on a monitor, so that an operation is carried out more efficiently. For example, it is assumed that the various medical devices and the monitor are connected via an internet protocol (IP) network using an IP converter or the like.

At this time, devices, such as an endoscope and a microscope, to be used during a diagnosis or an operation have a necessity that an image is displayed in real time so as to suit the sense of an operator; therefore, it has been required to achieve a series of multiple pieces of processing from image capturing to image display with low latency. With this configuration, it is expected that an operation can be carried out more efficiently.

For example, in a medical imaging apparatus disclosed in Patent Document 1, a configuration has been proposed, in which an IP converter that performs IP transmission of surgical images has an image processing function in an endoscopic surgery system or the like.

CITATION LIST

Patent Document

Patent Document 1: Japanese Patent Application Laid-Open No. 2019-162231

SUMMARY OF THE INVENTION

Problems to be Solved by the Invention

Meanwhile, conventionally, resynchronization of a frame rate has been executed on a monitor side in switching an image transmission path via an IP network in some cases and, as a result, medical information and the like have not been displayed on the monitor for a long period in some cases.

The present disclosure has been made in view of such a situation and is devised to enable reduction of a period in which medical information and the like are not displayed in switching an image transmission path.

Solutions to Problems

A medical-use control system according to one aspect of the present disclosure includes: a sending-side image converting apparatus configured to convert an image captured by a medical device into a transmission image to be transmitted via a network, and to send the image to the network; an image processing server configured to perform image processing on the image sent from the sending-side image converting apparatus via the network and to send an image generated by the image processing to the network; a receiving-side image converting apparatus configured to receive the transmission image and the image generated by the image processing via the network, to convert the transmission image and the image generated by the image processing into display images, and to output the display images to a display apparatus; and a delay time control unit configured to obtain a controlled delay time based on a difference between a delay time in a first transmission path without via the image processing server and a delay time in a second transmission path via the image processing server, on the basis of a characteristic of the display apparatus, and to control a timing at which the images are output to the display apparatus.

An image processing server according to one aspect of the present disclosure is an image processing server constituting a medical-use control system in conjunction with: a sending-side image converting apparatus configured to convert an image captured by a medical device into a transmission image to be transmitted via a network, and to send the image to the network; and a receiving-side image converting apparatus configured to receive the transmission image and the image generated by the image processing via the network, to convert the transmission image and the image generated by the image processing into display images, and to output the display images to a display apparatus, the image processing server including a delay time control unit configured to perform image processing on the image sent from the sending-side image converting apparatus via the network, to send an image generated by the image processing to the network, to obtain a controlled delay time based on a difference between a delay time in a first transmission path without via the image processing server and a delay time in a second transmission path via the image processing server, on the basis of a characteristic of the display apparatus, and to control a timing at which the images are output to the display apparatus.

An image converting apparatus according to one aspect of the present disclosure is a receiving-side image converting apparatus constituting a medical-use control system in conjunction with: a sending-side image converting apparatus configured to convert an image captured by a medical device into a transmission image to be transmitted via a network, and to send the image to the network; and an image processing server configured to perform image processing on the image sent from the sending-side image converting apparatus via the network and to send an image generated by the image processing to the network, the image converting apparatus including a delay time control unit configured to receive the transmission image and the image generated by the image processing via the network, to convert the transmission image and the image generated by the image processing into display images, to output the display images to a display apparatus, to obtain a controlled delay time based on a difference between a delay time in a first transmission path without via the image processing server and a delay time in a second transmission path via the image processing server, on the basis of a characteristic of the display apparatus, and to control a timing at which the images are output to the display apparatus.

A control method according to one aspect of the present disclosure includes causing a medical-use control system including: a sending-side image converting apparatus configured to convert an image captured by a medical device into a transmission image to be transmitted via a network, and to send the image to the network; an image processing server configured to perform image processing on the image sent from the sending-side image converting apparatus via the network and to send an image generated by the image processing to the network; and a receiving-side image converting apparatus configured to receive the transmission image and the image generated by the image processing via the network, to convert the transmission image and the image generated by the image processing into display images, and to output the display images to a display apparatus, to obtain a controlled delay time based on a difference between a delay time in a first transmission path without via the image processing server and a delay time in a second transmission path via the image processing server, on the basis of a characteristic of the display apparatus, and to control a timing at which the images are output to the display apparatus.

According to one aspect of the present disclosure, a medical-use control system includes: a sending-side image converting apparatus configured to convert an image captured by a medical device into a transmission image to be transmitted via a network, and to send the image to the network; an image processing server configured to perform image processing on the image sent from the sending-side image converting apparatus via the network and to send an image generated by the image processing to the network; and a receiving-side image converting apparatus configured to receive the transmission image and the image generated by the image processing via the network, to convert the transmission image and the image generated by the image processing into display images, and to output the display images to a display apparatus. Further, a controlled delay time based on a difference between a delay time in a first transmission path without via the image processing server and a delay time in a second transmission path via the image processing server is obtained on the basis of a characteristic of the display apparatus, and a timing at which the images are output to the display apparatus is controlled.

BRIEF DESCRIPTION OF DRAWINGS

FIG. 11 is a block diagram illustrating a configuration example of one embodiment of a computer to which the present technology is applied.

MODE FOR CARRYING OUT THE INVENTION

Figure 1:
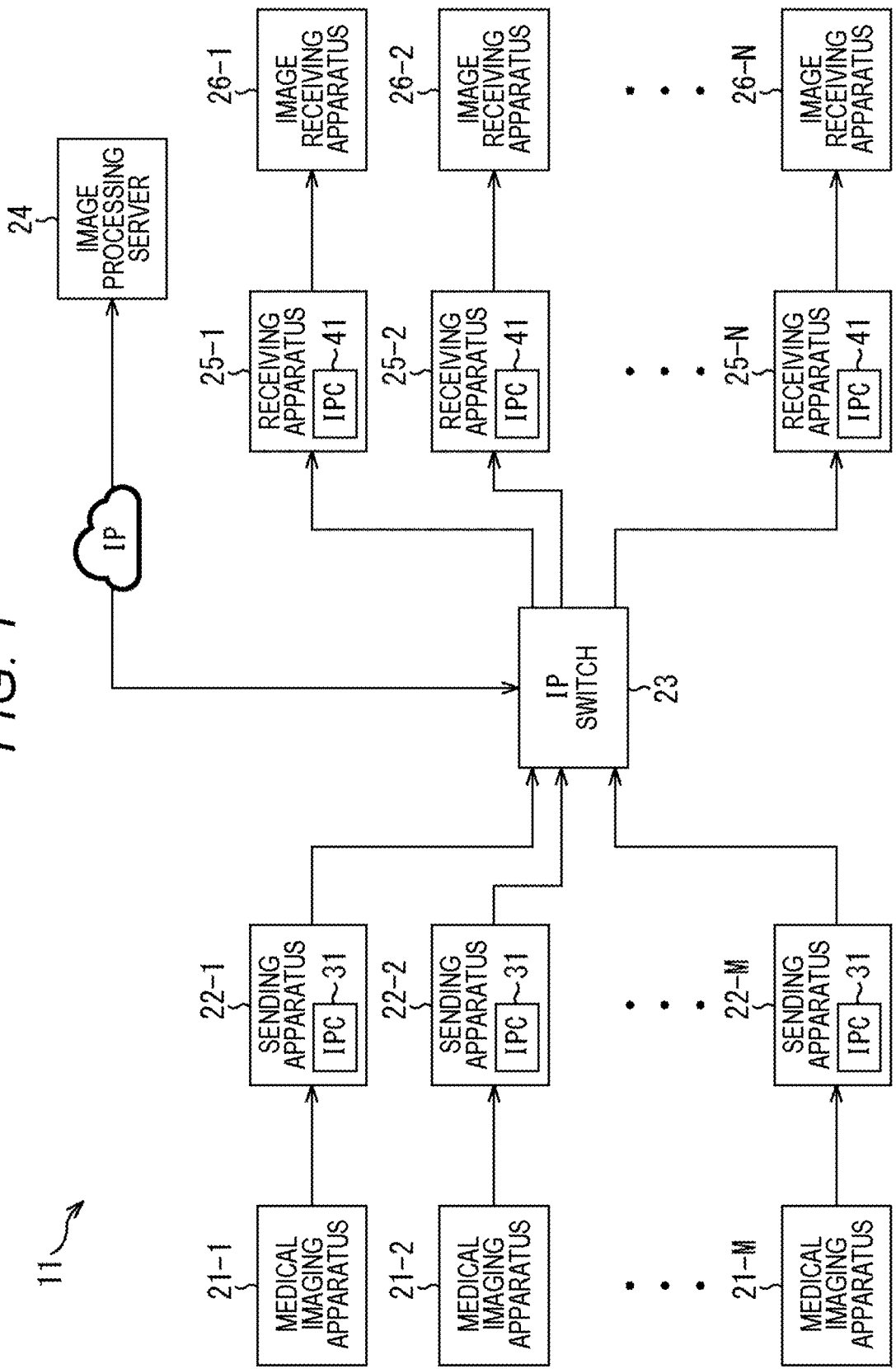
FIG. 1 is a block diagram illustrating a configuration example of one embodiment of a medical-use image transmission system to which the present technology is applied.

Hereinafter, specific embodiments to which the present technology is applied will be described in detail while referring to the drawings.

<Configuration Example of Medical-Use Image Transmission System>

FIG. 1 is a block diagram illustrating a configuration example of one embodiment of a medical-use image transmission system to which the present technology is applied.

As illustrated in FIG. 1, a medical-use image transmission system 11 includes M medical imaging apparatuses 21-1 to 21-M, M sending apparatuses 22-1 to 22-M, an IP switch 23, an image processing server 24, N receiving apparatuses 25-1 to 25-N, and N image receiving apparatuses 26-1 to 26-N.

The medical imaging apparatuses 21-1 to 21-M are apparatuses, such as an endoscope, an operating microscope, an X-ray image capturing apparatus, and an operative site camera, that capture images to be used for medical applications, and supply the images to the corresponding sending apparatuses 22-1 to 22-M, respectively. Note that the medical imaging apparatuses 21-1 to 21-M will be simply referred to as a medical imaging apparatus 21 below as appropriate in a case where they are not necessarily distinguished from one another.

The sending apparatuses 22-1 to 22-M IP-convert the images supplied from the corresponding medical imaging apparatuses 21-1 to 21-M, respectively, and transmit the images via the IP switch 23. Note that the sending apparatuses 22-1 to 22-M will be simply referred to as a sending apparatus 22 below as appropriate in a case where they are not necessarily distinguished from one another. Moreover, as illustrated in the figure, the sending apparatus 22 includes an IP converter 31 for IP-converting the image supplied from the medical imaging apparatus 21 into a transmission image to be transmitted via an IP network.

The IP switch 23 switches between an image transmission path between the sending apparatuses 22-1 to 22-M and the receiving apparatuses 25-1 to 25-N and an image transmission path via the image processing server 24. For example, the IP switch 23 is capable of switching between a transmission path (a first transmission path) for transmitting an image from the sending apparatus 22 to the receiving apparatus 25 without via the image processing server 24 and a transmission path (a second transmission path) for transmitting an image from the sending apparatus 22 to the receiving apparatus 25 via the image processing server 24.

The image processing server 24 is connected to the IP switch 23 via the IP network, performs various kinds of necessary image processing on an image that is captured by the medical imaging apparatus 21 and is supplied via the IP switch 23, and supplies the image to the IP switch 23.

The receiving apparatuses 25-1 to 25-N receive the IP-converted images supplied via the IP switch 23, reconstruct the original images (display images) from the images, and supply the display images to the corresponding image receiving apparatuses 26-1 to 26-N, respectively. Note that the receiving apparatuses 25-1 to 25-N will be simply referred to as a receiving apparatus 25 below as appropriate in a case where they are not necessarily distinguished from one another. Moreover, as illustrated in the figure, the receiving apparatus 25 includes an IP converter 41 for converting an image IP-converted as a transmission image into the original image.

The image receiving apparatuses 26-1 to 26-N receive the images supplied from the corresponding receiving apparatuses 25-1 to 25-N, respectively. For example, each of the image receiving apparatuses 26-1 to 26-N is a display that displays an image at a predetermined frame rate (e.g., 60 Hz), and is capable of receiving and displaying an image captured by the medical imaging apparatus 21. Note that the image receiving apparatuses 26-1 to 26-N will be simply referred to as an image receiving apparatus 26 below as appropriate in a case where they are not necessarily distinguished from one another.

Here, the receiving apparatus 25 and the image receiving apparatus 26 are connected in compliance with, for example, a standard such as HDMI (registered trademark) (an abbreviation of High-Definition Multimedia Interface) or Displayport and are capable of sending and receiving extended display identification data (EDID) which is device-specific identification data. With this configuration, the image receiving apparatus 26 is capable of notifying the receiving apparatus 25 of, for example, a frame rate.

In the medical-use image transmission system 11 configured as described above, a delay time refers to a period of time from a point in time when an image captured by the medical imaging apparatus 21 is input to the sending apparatus 22 to a point in time when the image is output from the receiving apparatus 25 to the image receiving apparatus 26. Further, in the medical-use image transmission system 11, a delay time in the transmission path without via the image processing server 24 and a delay time in the transmission path via the image processing server 24 differ depending on a time required for image processing in the image processing server 24.

For example, in the medical-use image transmission system 11, an image is transmitted to the image receiving apparatus 26 with low latency while multiple pieces of image processing are performed dynamically (i.e., in real time) by the image processing server 24, the IP converter 31, the IP converter 41, and the like. At this time, information of another external apparatus is shown while being superimposed on the image or the image is switched to another video in some cases in accordance with requests from an operator and the like; therefore, it is preferable to quickly perform the switching so as not to hinder a procedure. However, when a timing of a frame rate of the image receiving apparatus 26 deviates from a timing of an image signal received by the image receiving apparatus 26, the image receiving apparatus 26 needs to execute resynchronization processing of resynchronizing the frame rate in accordance with the image signal. For example, since the resynchronization processing may take a time from about several seconds to about several tens of seconds, there is a concern that a non-display period in which medical information cannot be displayed on the image receiving apparatus 26 may occur during the execution of the resynchronization processing.

Hence, the medical-use image transmission system 11 is capable of executing delay time control processing of controlling the delay time such that the timing at which the image is output from the receiving apparatus 25 coincides with the timing of the frame rate of the image receiving apparatus 26 even when the image transmission path is switched. With this configuration, the medical-use image transmission system 11 has no necessity that the image receiving apparatus 26 executes the resynchronization processing and, as a result, is capable of reducing the occurrence of the non-display period associated with the resynchronization processing (e.g., avoidance or reduction of the non-display period).

Here, with reference to FIGS. 2 to 6, a description will be given of a delay time occurring in an image transmitted via the IP network and processing in switching a transmission path, in the medical-use image transmission system 11.

Figure 2:
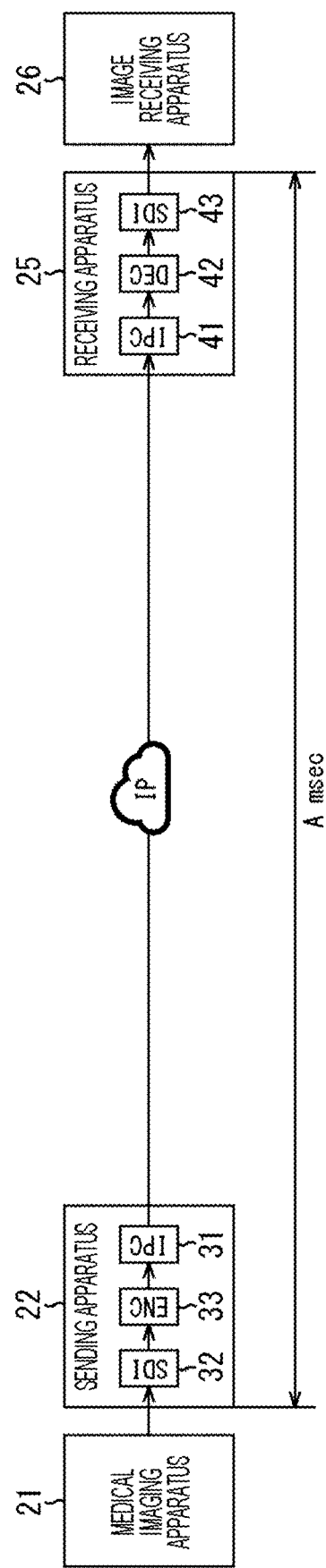
FIG. 2 is a diagram depicting a delay time in a transmission path without via an image processing server.

FIG. 2 is a diagram depicting a delay time in the transmission path where the sending apparatus 22 and the receiving apparatus 25 are connected via the IP network without via the image processing server 24.

The sending apparatus 22 includes an interface 32 and an encoder 33 in addition to the IP converter 31. The interface 32 acquires an image transmitted from the medical imaging apparatus 21 in compliance with, for example, a serial digital interface (SDI) standard and supplies the image to the encoder 33. The encoder 33 encodes the image and supplies the image to the IP converter 31.

The receiving apparatus 25 includes a decoder 42 and an interface 43 in addition to the IP converter 41. The decoder 42 decodes an image supplied from the IP converter 41 and supplies the image to the interface 43. The SDI 43 transmits the image to the image receiving apparatus 26 in compliance with, for example, the SDI standard.

Further, as illustrated in FIG. 2, A [msec] represents a delay time until an image input to the sending apparatus 22 is output from the receiving apparatus 25, in the transmission path where the sending apparatus 22 and the receiving apparatus 25 are connected via the IP network, without via the image processing server 24.

Figure 3:
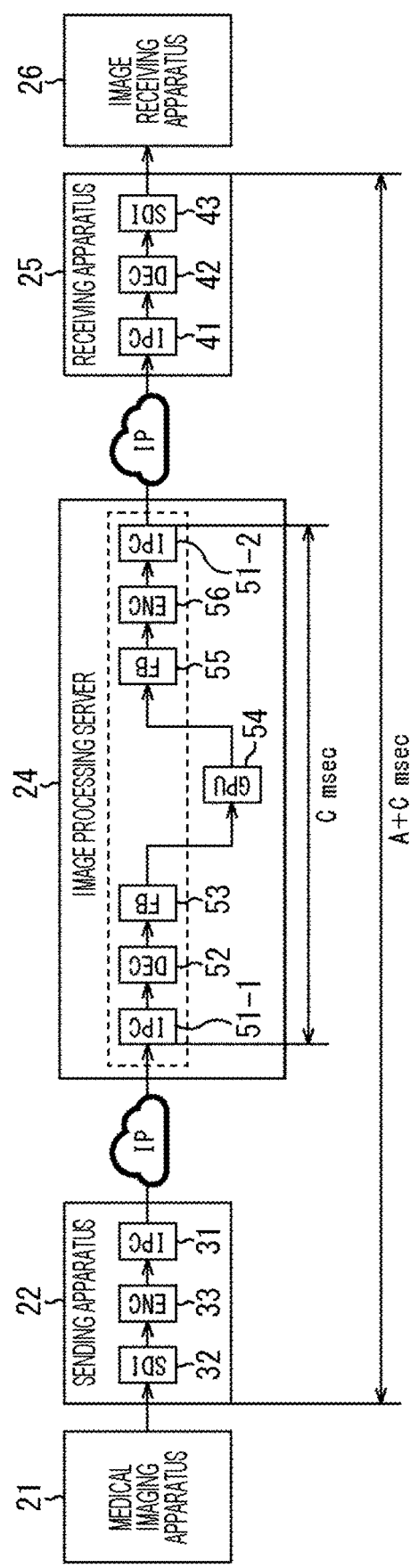
FIG. 3 is a diagram depicting a delay time in a transmission path via the image processing server in a case where delay time control processing is not performed.

FIG. 3 is a diagram depicting a delay time in the transmission path via the image processing server 24 in a case where the delay time control processing is not performed. Note that the sending apparatus 22 and the receiving apparatus 25 are identical with those in the configuration example described with reference to FIG. 2.

The image processing server 24 includes IP converters 51-1 and 51-2, a decoder 52, a frame buffer 53, an image processing unit 54, a frame buffer 55, and an encoder 56. Note that in the image processing server 24, the IP converters 51-1 and 51-2, the decoder 52, the frame buffer 53, the frame buffer 55, and the encoder 56 surrounded by a broken line constitute a network interface.

The IP converter 51-1 receives an IP-converted image sent from the sending apparatus 22 via the IP network, constructs the original image of the image, and supplies the original image to the decoder 52. The decoder 52 decodes the image supplied from the IP converter 51-1 and supplies the image to the frame buffer 53. The frame buffer 53 temporarily accumulates the image.

The image processing unit 54 is configured with, for example, a graphics processing unit (GPU), reads an image accumulated in the frame buffer 53, performs image processing on the image as necessary, and supplies the image after the image processing to the frame buffer 55.

The frame buffer 55 temporarily accumulates the image subjected to the image processing in the image processing unit 54. The encoder 56 encodes the image read from the frame buffer 55 and supplies the image to the IP converter 51-2. The IP converter 51-2 IP-converts the image and transmits the image to the receiving apparatus 25 via the IP network.

Further, as illustrated in FIG. 3, in the transmission path via the image processing server 24, a delay time until the image input to the sending apparatus 22 is output from the receiving apparatus 25 corresponds to a total delay time A+C [msec] obtained by adding an image processing delay time C [msec] until the image input to the image processing server 24 is output to the delay time A [msec] described with reference to FIG. 2.

Here, in a case where the image processing delay time C [msec] is not an integral multiple of the reciprocal of the frame rate of the image receiving apparatus 26, the image receiving apparatus 26 executes resynchronization processing of resynchronizing the frame rate in accordance with the timing at which the image is output from the receiving apparatus 25.

Figure 4:
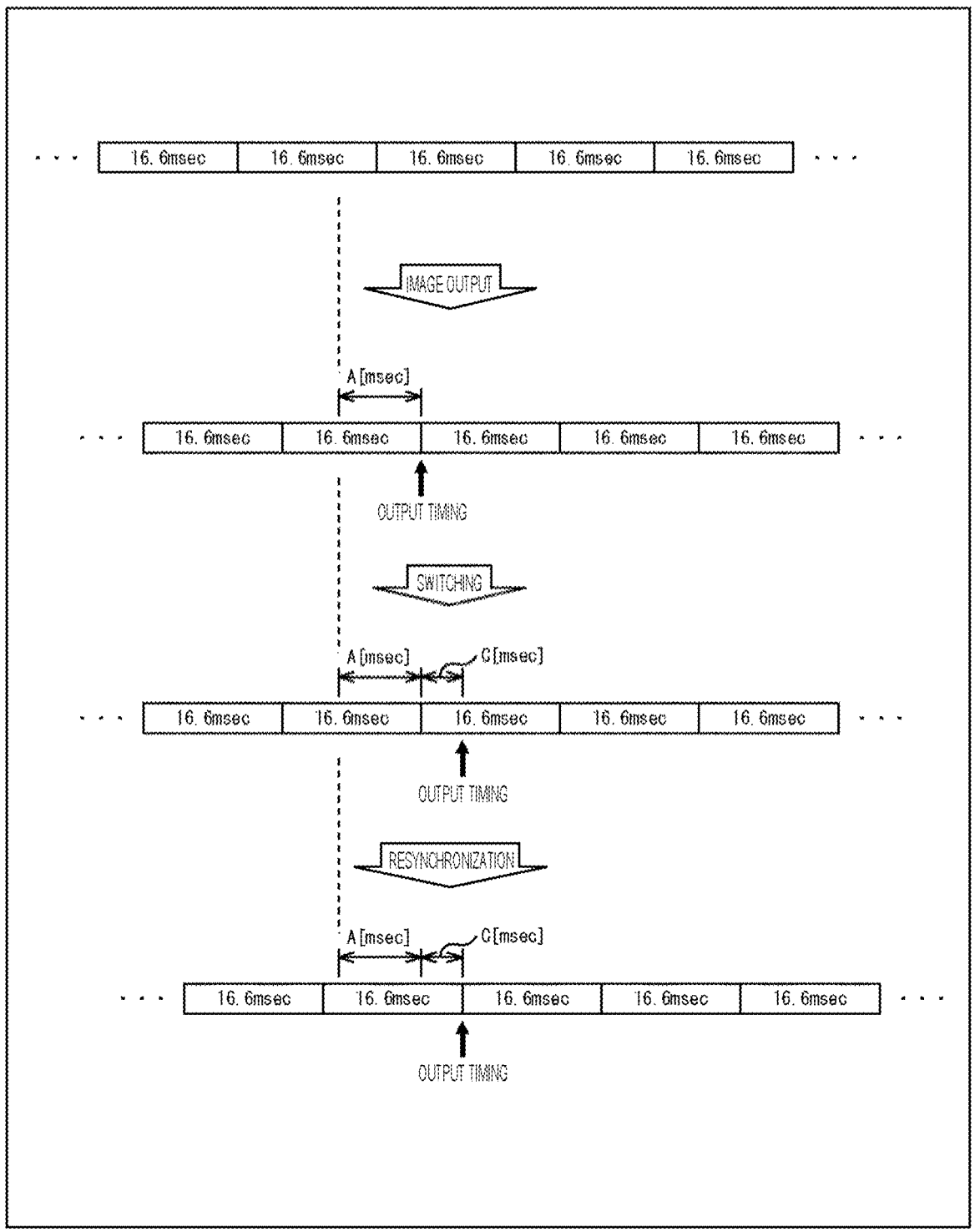
FIG. 4 is a diagram depicting processing in switching the transmission path in the case where the delay time control processing is not performed.

For example, with reference to FIG. 4, a description will be given of processing in switching the transmission path in the case where the delay time control processing is not performed, in a case where the frame rate of the image receiving apparatus 26 is 60 Hz.

In the case where the frame rate is 60 Hz, the image receiving apparatus 26 displays an image at an interval of 16.6 msec, which is the reciprocal of the frame rate. In the following description, the reciprocal of the frame rate is referred to as an image display interval.

First, when the image transmitted through the transmission path with the delay time A [msec], without via the image processing server 24 is output from the receiving apparatus 25, the image receiving apparatus 26 synchronizes the frame rate in accordance with the output timing of the delay time A [msec]. With this configuration, the image receiving apparatus 26 is capable of displaying the image output from the receiving apparatus 25 at the image display interval of 16.6 msec.

Thereafter, when switching to the transmission path via the image processing server 24 is made, the total delay time A+C [msec] is obtained and, as a result, the output timing at which the image is output from the receiving apparatus 25 deviates from the frame rate of the image receiving apparatus 26.

Therefore, the image receiving apparatus 26 is capable of displaying the image output from the receiving apparatus 25 at the image display interval of 16.6 msec by performing the resynchronization processing of resynchronizing the frame rate in accordance with the output timing of the total delay time A+C [msec].

Figure 5:
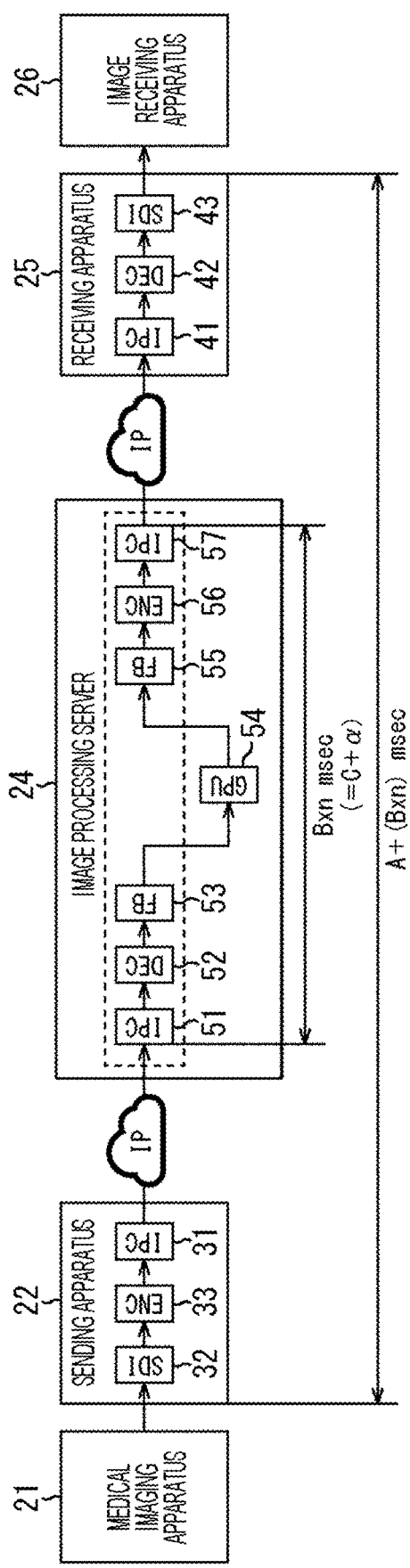
FIG. 5 is a diagram depicting a delay time in the transmission path via the image processing server in a case where the delay time control processing is performed.

FIG. 5 is a diagram depicting a delay time in the transmission path via the image processing server 24 in the case where the delay time control processing is performed. Note that the sending apparatus 22, the image processing server 24, and the receiving apparatus 25 are identical with those in the configuration example described with reference to FIG. 3.

As illustrated in FIG. 5, in the medical-use image transmission system 11, the delay time control processing is performed such that the delay time until the image input to the image processing server 24 is output becomes an integral multiple of an image display interval B which is the reciprocal of the frame rate of the image receiving apparatus 26. With this configuration, the image input to the image processing server 24 is output at a timing of a lapse of a controlled delay time B×n [msec] (n=integer).

For example, in the image processing server 24, the controlled delay time can be set by adjusting a time for temporarily accumulating images in the frame buffer 53 or 55. Note that since the time required for the image processing in the image processing server 24 is the same as that in a case where the delay time control processing is not performed, the controlled delay time B×n [msec] becomes equal to or more than the image processing delay time C [msec] (i.e., B×n=C+α).

Accordingly, in the transmission path via the image processing server 24, the delay time until the image input to the sending apparatus 22 is output from the receiving apparatus 25 is a controlled total delay time A+(B×n) [msec] obtained by adding the controlled delay time B×n [msec] until the image input to the image processing server 24 is output to the delay time A [msec] described with reference to FIG. 2. Note that the controlled delay time B×n [msec] is a difference between the delay time A [msec] of the transmission path without via the image processing server 24 and the controlled total delay time A+(B×n) [msec] of the transmission path via the image processing server 24.

Figure 6:
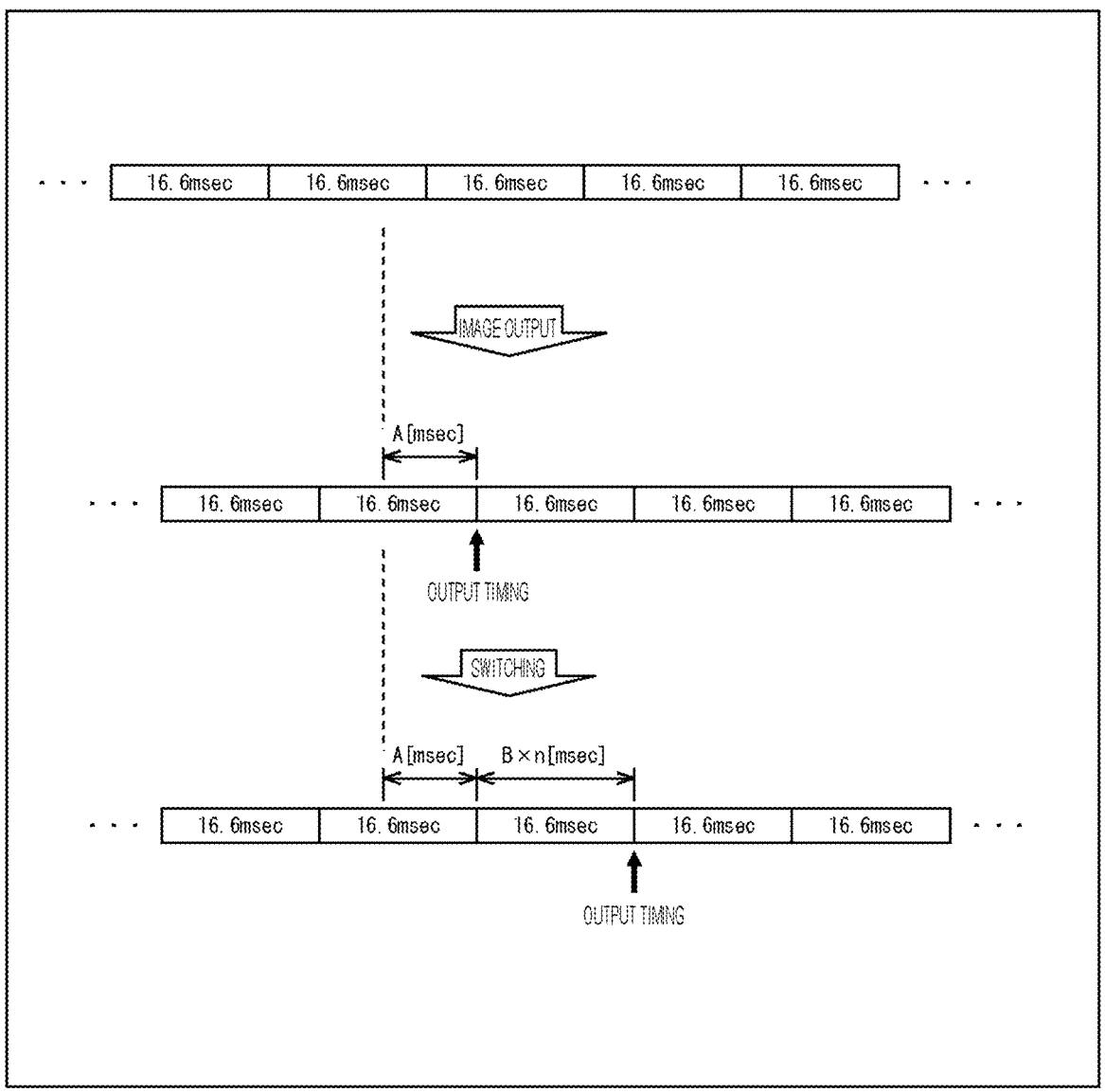
FIG. 6 is a diagram depicting processing in switching the transmission path in the case where the delay time control processing is performed.

Here, with reference to FIG. 6, a description will be given of processing in switching the transmission path in the case where the delay time control processing is performed, in the case where the frame rate of the image receiving apparatus 26 is 60 Hz.

In a manner similar to that described above with reference to FIG. 4, the image receiving apparatus 26 synchronizes the frame rate in accordance with the output timing at which the image transmitted through the transmission path via the image processing server 24 is output from the receiving apparatus 25.

Further, even when the switching to the transmission path via the image processing server 24 is made, the controlled total delay time A+(B×n) [msec] is obtained and, as a result, the output timing at which the image is output from the receiving apparatus 25 coincides with the frame rate of the image receiving apparatus 26. With this configuration, the image receiving apparatus 26 is capable of immediately displaying the image output from the receiving apparatus 25 at the image display interval of 16.6 msec, without the necessity to perform the resynchronization processing as described above.

Here, the delay time A [msec] is a design value, and in the delay time control processing, it is unnecessary to recognize the delay time A [msec] which is a delay amount of the IP network. Note that since the communication speed of the IP network is several microseconds, it is a negligible time. Moreover, the image processing delay time C [msec] is uniquely determined by a calculation amount of an application executed in the image processing server 24. For example, the image processing server 24 simultaneously sends time information when sending packets to the receiving apparatus 25, and the IP converter 41 is capable of achieving the synchronization on the basis of this time information.

<Delay Time Control Apparatus and Delay Time Control Processing>

Figure 7:
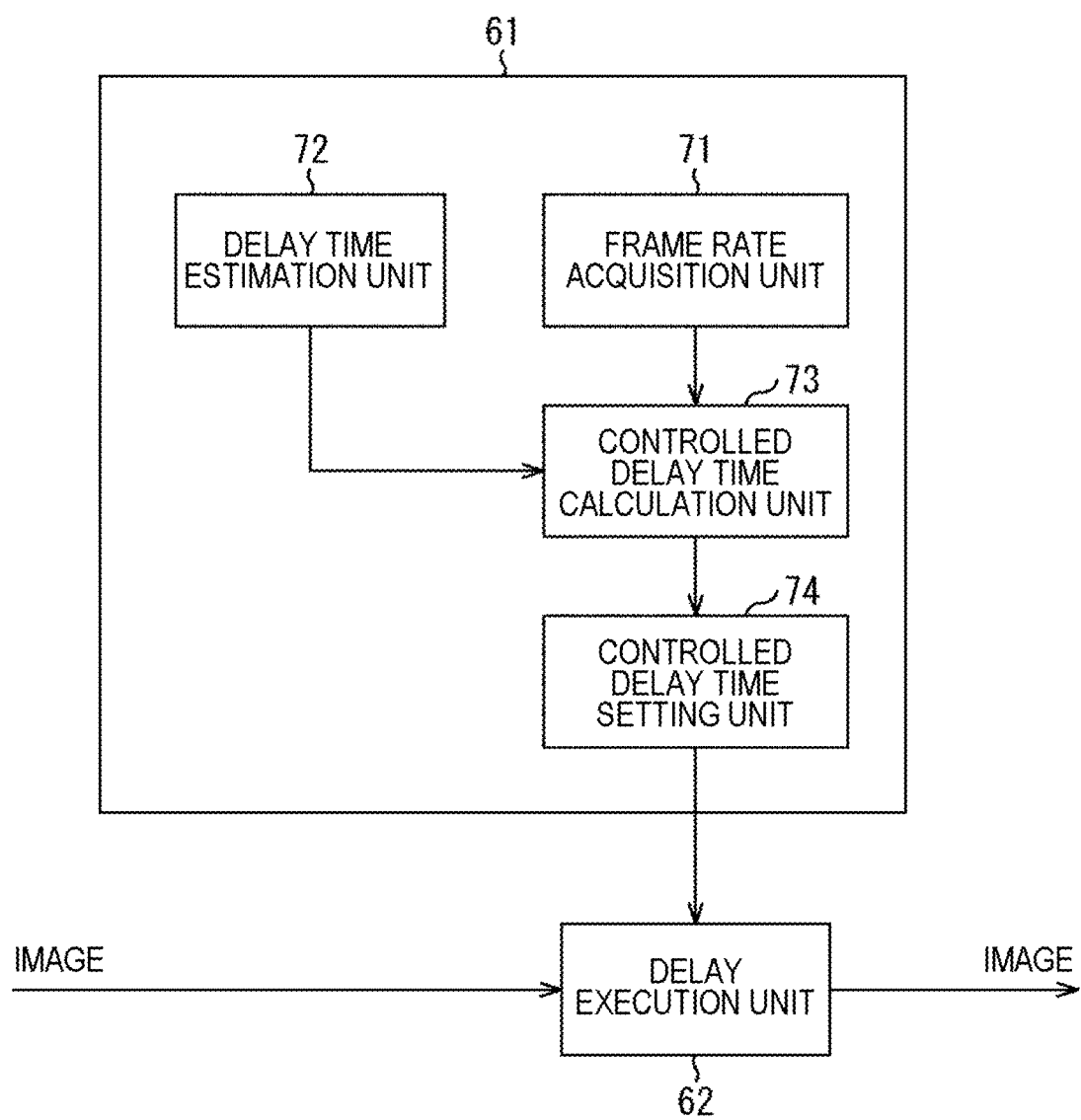
FIG. 7 is a block diagram illustrating a configuration example of a delay time control apparatus.

FIG. 7 is a block diagram illustrating a configuration example of a delay time control apparatus that executes the delay time control processing in the medical-use image transmission system 11.

As illustrated in FIG. 7, the delay time control apparatus 61 includes a frame rate acquisition unit 71, a delay time estimation unit 72, a controlled delay time calculation unit 73, and a controlled delay time setting unit 74. The delay time control apparatus 61 controls the delay time in a delay execution unit 62.

The frame rate acquisition unit 71 communicates with the image receiving apparatus 26 to acquire the frame rate notified from the image receiving apparatus 26, and supplies the image display interval B, which is the reciprocal of the frame rate, to the controlled delay time calculation unit 73.

The delay time estimation unit 72 estimates the image processing delay time C [msec] according to one or more pieces of image processing set to be executed in the image processing server 24, and supplies the image processing delay time C [msec] to the controlled delay time calculation unit 73.

Figure 8:
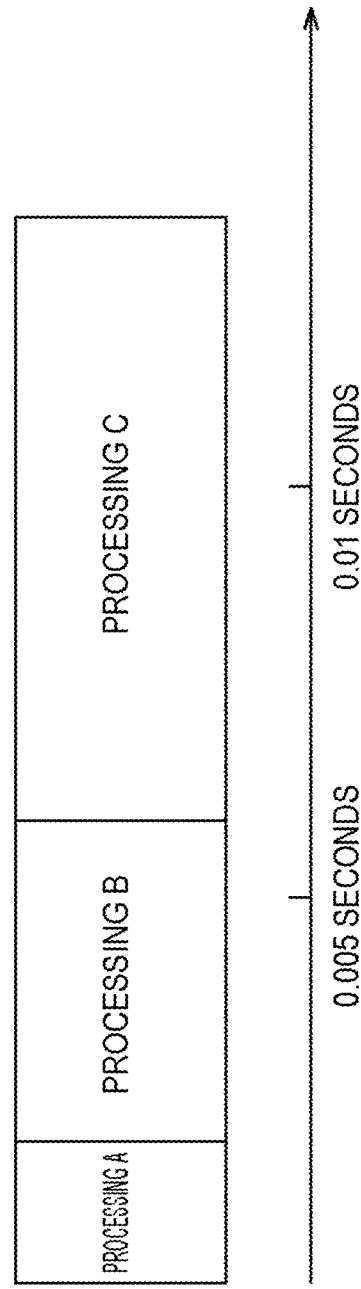
FIG. 8 is a diagram depicting an image processing delay time in a case where multiple pieces of image processing are performed.

Here, in a case where multiple pieces of image processing are performed in the image processing server 24, the delay time estimation unit 72 estimates the image processing delay time in accordance with a sum of times required for the respective pieces of image processing. For example, as illustrated in FIG. 8, in a case where three pieces of image processing A, B, and C are performed, the delay time estimation unit 72 estimates the image processing delay time in accordance with a sum of times required for the three pieces of image processing.

On the basis of the image display interval B notified from the frame rate acquisition unit 71 and the image processing delay time C [msec] notified from the delay time estimation unit 72, the controlled delay time calculation unit 73 calculates the controlled delay time B×n [msec] by determining an integer n such that the controlled delay time B×n [msec] becomes equal to or more than the image processing delay time C [msec].

The controlled delay time setting unit 74 sets the controlled delay time B×n [msec] calculated by the controlled delay time calculation unit 73, for the delay execution unit 62.

For example, as illustrated in FIG. 5 described above, in a case where the delay time is adjusted in the frame buffer 53 or 55, the delay execution unit 62 executes delay according to the controlled delay time B×n [msec] in the image processing server 24. Alternatively, the receiving apparatus 25 may include a frame buffer (not illustrated) serving as the delay execution unit 62. In this configuration, delay according to the controlled delay time B×n [msec] is executed in the receiving apparatus 25. That is, the delay execution unit 62 may be provided anywhere on the image transmission path via the image processing server 24 in the medical-use image transmission system 11.

For example, in a case where the IP converter 41 includes the delay execution unit 62, when images are displayed on the plurality of image receiving apparatuses 26, timings at which the images are output by the IP converters 41 of the corresponding receiving apparatuses 25, respectively, can be controlled in accordance with the controlled delay times based on the frame rates of the individual image receiving apparatuses 26. Accordingly, in this case, it is possible to easily perform the processing of displaying the image with the controlled delay time for each image receiving apparatus 26. For example, it is possible to reduce the complexity of the processing as compared with the configuration of performing the processing of controlling the timing of outputting the image in the image processing server 24.

Moreover, for example, in a case where the image processing server 24 includes the delay execution unit 62, when images are displayed on the plurality of image receiving apparatuses 26, the timing of outputting the images can be controlled in accordance with the same controlled delay time for these image receiving apparatuses 26. At this time, as the controlled delay time, for example, the longest controlled delay time among the controlled delay times based on the frame rates of the individual image receiving apparatuses 26 can be used. In this manner, by controlling the timing of outputting the images to the plurality of image receiving apparatuses 26 in accordance with the identical controlled delay time, it is possible to reduce the occurrence of a deviation in the images displayed by these image receiving apparatuses 26. For example, it is possible to suppress a medical staff from feeling uncomfortable.

Likewise, the delay time control apparatus 61 is also capable of having the configuration of any of the respective apparatuses constituting the medical-use image transmission system 11. For example, the medical-use image transmission system 11 is capable of adopting a configuration in which the image processing server 24 includes the delay execution unit 62, a configuration in which the receiving apparatus 25 includes the delay execution unit 62, or the like. Note that, in a case where the image processing server 24 includes the delay time control apparatus 61, it is necessary to have a configuration in which the receiving apparatus 25 acquires the frame rate from the image receiving apparatus 26 and the frame rate is notified from the receiving apparatus 25 to the image processing server 24.

As described above, the delay time control apparatus 61 performs control such that the delay time in the delay execution unit 62 becomes the controlled delay time B×n [msec], and thus, even when the transmission path without via the image processing server 24 and the transmission path via the image processing server 24 are switched, it is possible to avoid execution of the resynchronization processing in the image receiving apparatus 26. As a result, in the image receiving apparatus 26, a non-display period does not occur in switching the transmission path. For example, it is possible to reduce occurrence of a state that hinders a procedure of an operator or the like.

Moreover, in the medical-use image transmission system 11, as illustrated in FIG. 8, the time required for processing for each of the plurality of pieces of image processing may be presented to a user with a graphical user interface (GUI) of a bar graph as illustrated. With this configuration, the user is able to select image processing to be executed by the image processing server 24 through the GUI with reference to the time required for each piece of image processing. In this manner, by visualizing which image processing causes delay, for each delay time, the medical staff is able to determine which image processing is not to be performed in a case where the delay is desired to be reduced.

Figure 9:
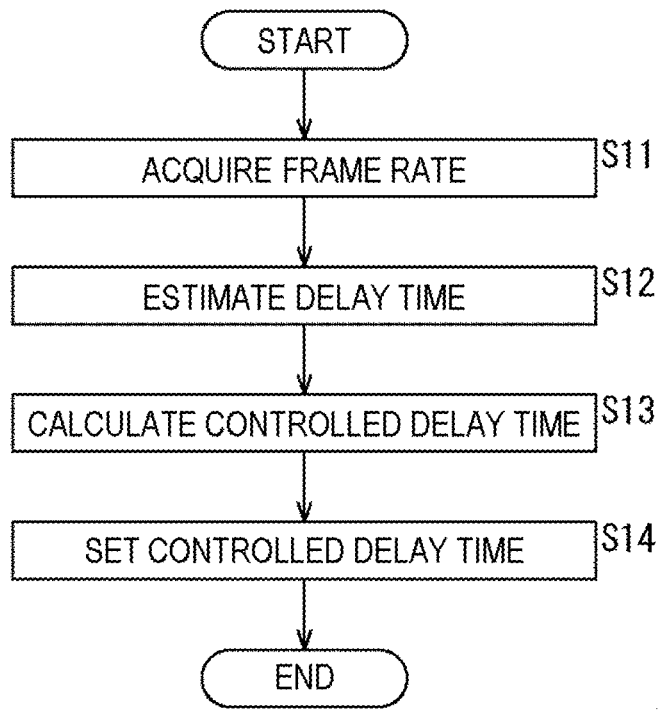
FIG. 9 is a flowchart depicting the delay time control processing.

FIG. 9 is a flowchart depicting the delay time control processing executed in the delay time control apparatus 61.

For example, the processing is started at a timing when the medical-use image transmission system 11 starts up. In step S11, the frame rate acquisition unit 71 communicates with the image receiving apparatus 26 and acquires the frame rate notified from the image receiving apparatus 26. Then, the frame rate acquisition unit 71 supplies the image display interval B which is the reciprocal of the acquired frame rate, to the controlled delay time calculation unit 73.

In step S12, the delay time estimation unit 72 estimates the image processing delay time C [msec] according to the image processing set to be executed in the image processing server 24, and supplies the image processing delay time C [msec] to the controlled delay time calculation unit 73.

In step S13, on the basis of the image display interval B notified from the frame rate acquisition unit 71 in step S11 and the image processing delay time C [msec] notified from the delay time estimation unit 72 in step S12, the controlled delay time calculation unit 73 calculates the controlled delay time B×n [msec] by determining the integer n such that the controlled delay time B×n [msec] becomes equal to or more than the image processing delay time C [msec].

In step S14, the controlled delay time setting unit 74 sets the controlled delay time B×n [msec] calculated by the controlled delay time calculation unit 73 in step S13, for the delay execution unit 62. Thereafter, the processing ends.

As described above, the delay time control apparatus 61 is capable of setting the controlled delay time B×n [msec] for the delay execution unit 62 such that the controlled delay time B×n [msec] becomes the integral multiple of the reciprocal of the frame rate. That is, the delay time control apparatus 61 is capable of obtaining the controlled delay time B×n [msec] based on the difference between the delay time in the transmission path without via the image processing server 24 and the delay time in the transmission path via the image processing server 24, on the basis of the frame rate which is the characteristic of the image receiving apparatus 26, and is capable of controlling the timing at which the image is output from the receiving apparatus 25 to the image receiving apparatus 26. With this configuration, it is possible to reduce the state in which medical information and the like are not displayed when the IP switch 23 switches between the transmission path without via the image processing server 24 and the transmission path via the image processing server 24.

Note that the delay time control apparatus 61 may acquire the information of the medical imaging apparatus 21 connected to the sending apparatus 22 and set the controlled delay time on the basis of the characteristic of the medical imaging apparatus 21. For example, since it is important for an endoscope and a microscope to have real-time qualities, the delay time control apparatus 61 determines a priority for each medical imaging apparatus 21, and sets a controlled delay time such that the medical imaging apparatus 21 with a higher priority has the lowest latency or sets the controlled delay time such that the medical imaging apparatus 21 with a higher priority does not cause delay. Conversely, the delay time control apparatus 61 sets a controlled delay time by lowering the priority for the medical imaging apparatus 21, such as an operative site camera, that causes no problem even if it causes delay in some degree.

Moreover, the delay time control apparatus 61 is capable of adjusting the controlled delay time in accordance with the processing of the application executed by the image processing server 24 or the IP converter 41. This is because it is assumed that the calculation amount of the application executed by the image processing server 24 or the IP converter 41 varies. For example, in a case where the calculation amount of the application is large, the controlled delay time may be adjusted to be decreased. In a case where the processing of the application cannot be executed in time even when the controlled delay time is decreased, conversely, the controlled delay time may be adjusted to be increased.

In addition, the delay time control apparatus 61 may set the controlled delay time so as to cause delay of two frames constantly, and adjust the controlled delay time so as to decrease the controlled delay time in accordance with the worst case. At this time, in a case where the controlled delay time is excessively increased, it is preferable to make a notification about this excessive increase and urge the medical staff to stop the processing that has caused the increase in the controlled delay time. Specifically, in a situation in which the use of an electric scalpel produces a large amount of smoke, the processing time in the image processing server 24 may increase in a case where a calculation amount of smoke removal processing increases. At this time, an adjustment to decrease the conventional controlled delay time is made in accordance with the increased processing time.

Furthermore, in a case where the resynchronization processing of the frame rate is executed in the image receiving apparatus 26, the delay time control apparatus 61 is capable of resetting the controlled delay time in accordance with the frame rate after the resynchronization. For example, in a case where the image receiving apparatus 26 restarts, information on the restart is notified from the image receiving apparatus 26 to the receiving apparatus 25, and the delay time control apparatus 61 is capable of resetting the controlled delay time in accordance with this notification. Moreover, in a case where no power is supplied to the image receiving apparatus 26 or the image receiving apparatus 26 and the receiving apparatus 25 are disconnected, the delay time control apparatus 61 may stop the delay time control processing until the frame rate is notified from the image receiving apparatus 26.

Moreover, in the medical-use image transmission system 11, it is assumed that various medical devices such as an endoscope, a microscope, an ultrasonic apparatus, and a magnetic resonance imaging (MRI) apparatus are used as the medical imaging apparatuses 21. In this case, when the frame rates output from the respective medical imaging apparatuses 21 are different from one another, the delay time control apparatus 61 preferably executes the delay time control processing in accordance with the image receiving apparatus 26. That is, the delay time control apparatus 61 is capable of setting the controlled delay time in accordance with the characteristic of the medical imaging apparatus 21 and the characteristic of the image receiving apparatus 26.

For example, in a case where the image processing unit 54 is incapable of performing processing at 60 frames per second (fps) in terms of signal processing, the image processing unit 54 performs the processing at 29.97 fps and outputs images two by two. Moreover, when the image processing unit 54 has the ability to perform the processing at 60 fps and an image with a high processing load is to be processed, the image processing unit 54 does not output images to the image receiving apparatus 26 at 30 fps, but processes images at 30 fps, adds one copy, and outputs the images to the image receiving apparatus 26 at 60 fps. That is, in a case where the ultrasound apparatus which is the medical imaging apparatus 21 outputs images at 30 fps and the frame rate of the image receiving apparatus 26 is 60 fps, the image processing unit 54 is capable of adding a copy and outputting the images at 60 fps while processing the images at 30 fps.

The frame rate acquisition unit 71 may acquire the characteristic of the image receiving apparatus 26, for example, in addition to acquiring the frame rate from the image receiving apparatus 26. For example, the frame rate acquisition unit 71 is capable of holding a table in which the type and frame rate of the image receiving apparatus 26 are associated with each other, thereby acquiring the type of the image receiving apparatus 26 and acquiring the frame rate while referring to the table. Alternatively, the delay time control apparatus 61 may be configured such that a preset frame rate is input as a characteristic of the image receiving apparatus 26. For example, a nurse may input a frame rate determined by examining the image receiving apparatus 26.

As described above, various methods can be used as a method of acquiring a frame rate.

APPLICATION EXAMPLES

The technology according to the present disclosure is applicable to various products. For example, the technology according to the present disclosure may be applied to an operating room system.

Figure 10:
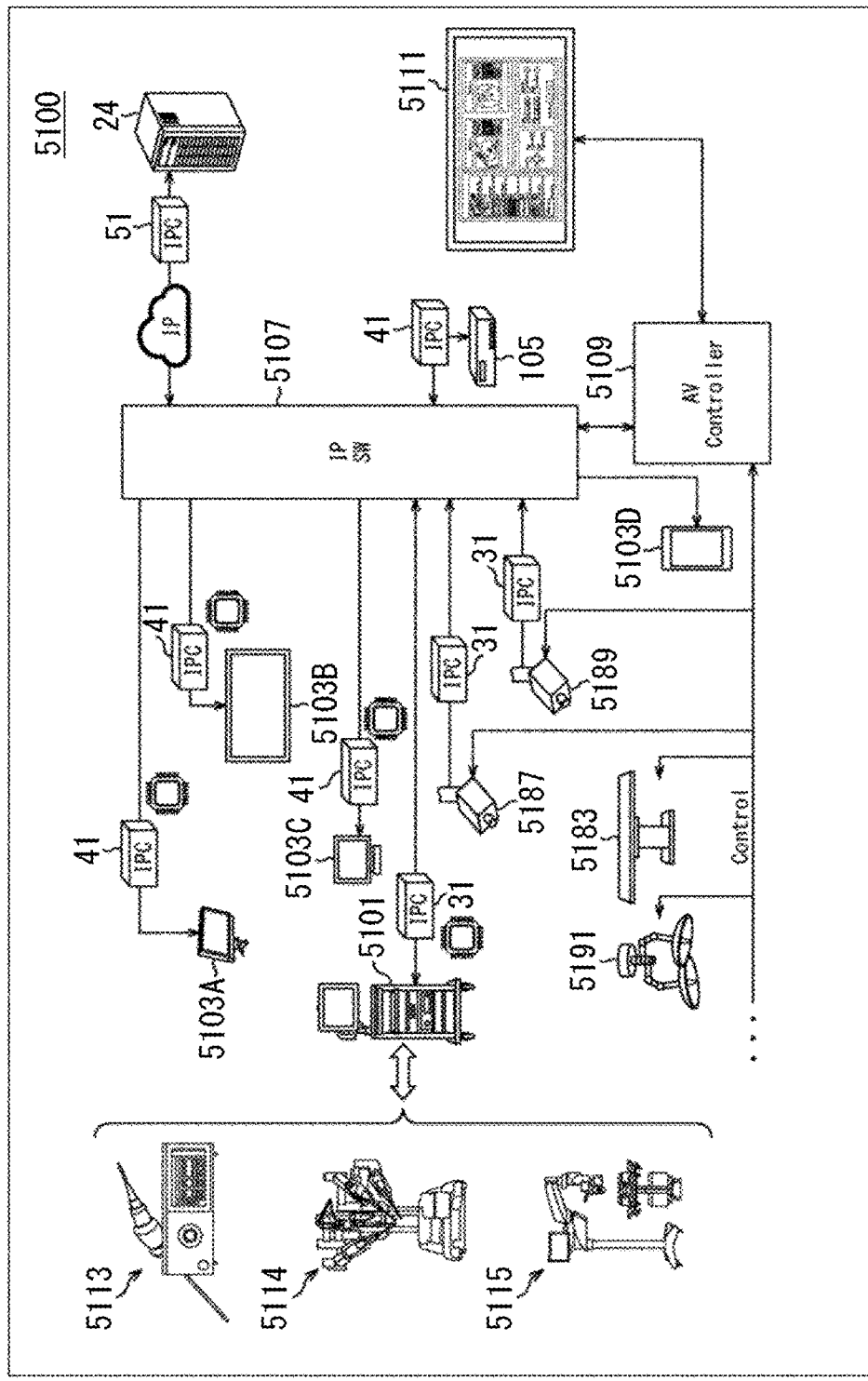
FIG. 10 is a diagram schematically illustrating a general configuration of an operating room system.

FIG. 10 is a diagram schematically illustrating a general configuration of an operating room system 5100 to which the technology according to the present disclosure can be applied. Referring to FIG. 10, the operating room system 5100 is configured in such a manner that apparatuses installed in an operating room are cooperatively connected to each other via an IP switch 5107 and an audiovisual controller (AV controller) 5109. This operating room system is configured with an IP network capable of sending and receiving 4K/8K video, and input/output video and control information for each device are sent and received via the IP network.

Various apparatuses may be installed in the operating room. FIG. 10 illustrates, as an example, a group of various apparatuses 5101 for an endoscopic operation, a ceiling camera 5187 that is provided on the ceiling of the operating room and captures an image of the hands of an operator, an operative site camera 5189 that is provided on the ceiling of the operating room and captures an image of the entire operating room, a plurality of display apparatuses 5103A to 5103D, a recorder 5105, a patient bed 5183, and a lighting fixture 5191.

The IP converter 31 IP-converts video from each medical image capturing apparatus (e.g., an endoscope, an operating microscope, an X-ray image capturing apparatus, an operative site camera) and sends the video onto the network. The monitor-side IP converter 41 converts a format of the video transmitted via the network into a format unique to the monitor, and outputs the video. This IP converter 41 may have various image processing functions, and these image processing functions may include resolution conversion processing depending on an output destination, rotation/hand-induced camera shake correction of endoscopic video, object recognition processing, and the like. Moreover, these image processing functions may include partial processing such as feature information extraction for analysis by the image processing server 24. These image processing functions may be unique to the connected medical image apparatus or may be upgradable from the outside. The display-side IP converter 41 is also capable of performing processing such as synthesis of a plurality of videos (e.g., PinP processing) and superimposition of annotation information.

Here, among these apparatuses, the group of apparatuses 5101 belongs to an endoscopic operation system 5113, and includes an endoscope, a display apparatus that displays an image captured by the endoscope, and the like. Each apparatus belonging to the endoscopic operation system 5113 is also referred to as a medical-use device. On the other hand, the display apparatuses 5103A to 5103D, the recorder 5105, the patient bed 5183, and the lighting fixture 5191 are apparatuses provided in, for example, the operating room separately from the endoscopic operation system 5113. Each apparatus not belonging to the endoscopic operation system 5113 is also referred to as a non-medical-use device. The IP switch 5107 and/or the audiovisual controller 5109 control(s) the operations of the medical devices and non-medical devices in cooperation with each other.

Likewise, in a case where the group of apparatuses 5101 includes medical image acquisition apparatuses such as an operating robot (an operative master-slave) system 5114 and an X-ray imaging apparatus 5115 in the operating room as illustrated in the figure, these devices may also be connected.

The audiovisual controller 5109 controls processing related to image display in the medical devices and non-medical devices in a centralized manner. Specifically, among the apparatuses included in the operating room system 5100, the group of apparatuses 5101, the ceiling camera 5187, and the operative site camera 5189 can be apparatuses (hereinafter, also referred to as originating-source apparatuses) having a function of originating information to be displayed during an operation (hereinafter, also referred to as display information). Moreover, the display apparatuses 5103A to 5103D can be apparatuses (hereinafter, also referred to as output-destination apparatuses) to which display information is output. Moreover, the recorder 5105 may be an apparatus corresponding to both the originating-source apparatus and the output-destination apparatus. The audiovisual controller 5109 has a function of controlling operations of the originating-source apparatus and output-destination apparatus, acquiring display information from the originating-source apparatus, sending the display information to the output-destination apparatus, and displaying or recording the display information. Note that the display information includes various images captured during an operation, various kinds of information on an operation (e.g., physical information of a patient, past examination results, information on an operation procedure, and the like), and the like.

Specifically, information on an image of an operative site in the body cavity of the patient captured by the endoscope can be sent as the display information from the group of apparatuses 5101 to the audiovisual controller 5109. Moreover, information on an image of the hands of the operator captured by the ceiling camera 5187 can be sent as the display information from the ceiling camera 5187. Moreover, information on an image indicating the state of the entire operating room captured by the operative site camera 5189 can be sent as the display information from the operative site camera 5189. Note that in a case where there is another apparatus having an image capturing function in the operating room system 5100, the audiovisual controller 5109 may also acquire information on an image captured by the other apparatus as the display information from the other apparatus.

Alternatively, for example, multiple pieces of information on these images captured in the past are recorded in the recorder 5105 by the audiovisual controller 5109. The audiovisual controller 5109 is capable of acquiring the multiple pieces of information on the images captured in the past from the recorder 5105 as the display information. Note that various kinds of information regarding an operation may also be recorded in the recorder 5105 in advance.

The audiovisual controller 5109 causes at least one of the display apparatuses 5103A to 5103D, which are output-destination apparatuses, to display the acquired display information (that is, images captured during an operation and various kinds of information regarding an operation). In the illustrated example, the display apparatus 5103A is a display apparatus installed to be suspended from the ceiling of the operating room, the display apparatus 5103B is a display apparatus installed on a wall surface of the operating room, the display apparatus 5103C is a display apparatus installed on a desk in the operating room, and the display apparatus 5103D is a mobile device (for example, a tablet personal computer (PC)) having a display function.

Moreover, the operating room system 5100 may include an apparatus outside the operating room. The apparatus outside the operating room may be, for example, a server connected to a network constructed inside and outside a hospital, a PC used by a medical staff, a projector installed in a meeting room of the hospital, or the like. In a case where such an external apparatus is outside the hospital, the audiovisual controller 5109 is also capable of causing a display apparatus of another hospital to display the display information via a video conference system or the like for telemedicine.

Moreover, the server or cloud outside the operating room may be used for image analysis and data analysis, and may be used to send video information in the operating room to an external server, generate additional information by big data analysis or recognition/analysis processing using AI (machine learning) on the server side, and feed the additional information back to the display apparatus in the operating room. In this case, an IP converter connected to a video device in the operating room sends data to the server and analyzes the video. The data to be sent may be a video of an operation itself obtained from an endoscope or the like, metadata extracted from the video, data indicating an on-the-job status of a connected device, or the like.

Note that an operating room control apparatus (not illustrated) controls processing other than processing related to image display in the non-medical device, in a centralized manner. For example, the operating room control apparatus controls driving of the patient bed 5183, ceiling camera 5187, operative site camera 5189, and lighting fixture 5191.

The operating room system 5100 is provided with a central console panel 5111, and the user is able to give an instruction regarding image display such as switching of input/output devices to the audiovisual controller 5109 or give an instruction regarding action of the non-medical devices to the operating room control apparatus, via the central console panel 5111. The central console panel 5111 is configured with a touch panel provided on a display surface of a display apparatus.

The technology according to the present disclosure is suitably applicable to the image processing server 24 or the IP converter 41, among the configurations described above. With this configuration, when switching to the transmission path via the image processing server 24 is made by the IP switch 5107, as described above, execution of resynchronization in the display apparatuses 5103A to 5103D is avoided, and image switching can be made instantaneously. As a result, it is possible to reduce the time during which the medical information cannot be displayed on the display apparatuses 5103A to 5103D. For example, it is possible to eliminate a state that hinders the procedure of the operator or the like.

<Configuration Example of Computer>

Next, the foregoing series of pieces of processing (the control method) can be performed by hardware or can be performed by software. In a case where the series of pieces of processing is performed by software, a program constituting the software is installed in a general-purpose computer or the like.

FIG. 11 is a block diagram illustrating a configuration example of one embodiment of a computer in which a program for executing the above-described series of pieces of processing is installed.

The program can be recorded in advance in a hard disk 105 or a ROM 103 as a recording medium incorporated in the computer.

Alternatively, the program can be stored (recorded) in a removable recording medium 111 to be driven by a drive 109. Such a removable recording medium 111 can be provided in the form of packaged software. Here, examples of the removable recording medium 111 include a flexible disk, a compact disc read only memory (CD-ROM), a magneto optical (MO) disk, a digital versatile disc (DVD), a magnetic disk, a semiconductor memory, and the like.

Note that the program can be installed in the computer from the removable recording medium 111 as described above, or can be downloaded to the computer via a communication network or a broadcast network and installed in the hard disk 105 incorporated in the computer. That is, for example, the program can be transferred in a wireless manner from a download site to the computer via an artificial satellite for digital satellite broadcasting, or can be transferred in a wired manner to the computer via a network such as a local area network (LAN) or the Internet.

The computer incorporates a central processing unit (CPU) 102, and an input/output interface 110 is connected to the CPU 102 via a bus 101.

When a command is input to the CPU 102 via the input/output interface 110 in such a manner that, for example, a user manipulates an input unit 107, the CPU 102 executes a program stored in the read only memory (ROM) 103 in accordance with the command. Alternatively, the CPU 102 loads the program stored in the hard disk 105 into a random access memory (RAM) 104 and executes the program.

With this configuration, the CPU 102 performs the pieces of processing according to the foregoing flowchart or the pieces of processing performed by the configurations illustrated in the foregoing block diagram. Then, the CPU 102 outputs the processing result from the output unit 106, sends the processing result from the communication unit 108, or records the processing result in the hard disk 105 via the input/output interface 110, for example, as necessary.

Note that the input unit 107 includes a keyboard, a mouse, a microphone, and the like. Moreover, the output unit 106 includes a liquid crystal display (LCD), a speaker, and the like.

Here, in the present specification, the pieces of processing performed by the computer in accordance with the program are not necessarily performed in a time series manner in the order described as the flowchart. That is, the pieces of processing performed by the computer in accordance with the program also include pieces of processing to be executed in parallel or independently of one another (e.g., parallel processing or processing by an object).

Moreover, the program may be processed by a single computer (processor) or may be processed by a plurality of computers in a distributed manner. Furthermore, the program may be transferred to and executed by a remote computer.

Furthermore, the term "system" in the present specification refers to an aggregate of a plurality of constituent elements (apparatuses, modules (components), and the like), and it does not matter whether or not all the constituent elements are in the same housing. Therefore, the term "system" involves both of a plurality of apparatuses accommodated in separate housings and connected to one another via a network and a single apparatus in which a plurality of modules is accommodated in a single housing.

Moreover, for example, a configuration described as a single apparatus (or a single processing unit) may be divided and configured as a plurality of apparatuses (or a plurality of processing units). Conversely, configurations described above as a plurality of apparatuses (or a plurality of processing units) may be collectively configured as a single apparatus (or a single processing unit). As a matter of course, moreover, a configuration other than the foregoing configurations may be added to the configuration of each apparatus (or each processing unit). Furthermore, as long as the configurations and actions as the entire system are substantially the same, a part of the configuration of a certain apparatus (or a certain processing unit) may be included in the configuration of another apparatus (or another processing unit).

Moreover, for example, the present technology can take a configuration of cloud computing in which a plurality of apparatuses processes one function via a network in collaboration with one another on a task-sharing basis.

Moreover, for example, the foregoing program can be executed in any apparatus. In that case, it is sufficient that the apparatus has a necessary function (e.g., a functional block) and can obtain necessary information.

Moreover, for example, the respective steps described with reference to the foregoing flowcharts can be executed by a single apparatus or can be executed by a plurality of apparatuses with the steps divided among the plurality of apparatuses. Furthermore, in a case where one step includes multiple pieces of processing, the multiple pieces of processing included in the one step can be carried out by a single apparatus or can be carried out by a plurality of apparatuses with the multiple pieces of processing divided among the plurality of apparatuses. In other words, multiple pieces of processing included in one step can also be executed as pieces of processing in multiple steps. Conversely, the pieces of processing described as the multiple steps can be collectively executed as one step.

Note that, in the program executed by the computer, the pieces of processing in the steps describing the program may be executed in a time series manner in the order described in the present specification, or may be executed in parallel or independently of one another at a necessary timing such as a time when a program is called up. That is, as long as there is no contradiction, the processing in each step may be executed in an order different from the foregoing order. Furthermore, the pieces of processing in the steps describing this program may be executed in parallel with multiple pieces of processing of another program, or may be executed in combination with the multiple pieces of processing of another program.

Note that a plurality of the present technologies described in the present specification can be implemented independently as a single body as long as there is no contradiction. Of course, any of the plurality of present technologies can be used in combination. For example, a part of or all of the present technologies described in any of the embodiments can be implemented in combination with a part of or all of the present technologies described in another embodiment. Moreover, a part of or all of the foregoing present technologies may be implemented in combination with another technology not described above.

<Combination Examples of Configurations>

Note that the present technology can also adopt the following configurations.

(1)

A medical-use control system including:

a sending-side image converting apparatus configured to convert an image captured by a medical device into a transmission image to be transmitted via a network, and to send the image to the network;

an image processing server configured to perform image processing on the image sent from the sending-side image converting apparatus via the network and to send an image generated by the image processing to the network;

a receiving-side image converting apparatus configured to receive the transmission image and the image generated by the image processing via the network, to convert the transmission image and the image generated by the image processing into display images, and to output the display images to a display apparatus; and a delay time control unit configured to obtain a controlled delay time based on a difference between a delay time in a first transmission path without via the image processing server and a delay time in a second transmission path via the image processing server, on the basis of a characteristic of the display apparatus, and to control a timing at which the images are output to the display apparatus.

(2)

The medical-use control system as recited in (1), in which the delay time control unit obtains the controlled delay time by acquiring a frame rate of the display apparatus as the characteristic, and sets the controlled delay time for a delay execution unit provided on the second transmission path.

(3)

The medical-use control system as recited in (2), in which the delay time control unit obtains the controlled delay time that is an integral multiple of a reciprocal of the frame rate of the display apparatus.

(4)

The medical-use control system as recited in (3), in which the delay time control unit calculates the controlled delay time by determining an integer such that the controlled delay time becomes equal to or more than an image processing delay time estimated from one or more pieces of image processing set to be executed in the image processing server.

(5)

The medical-use control system as recited in any of (2) to (4), in which the delay execution unit is a frame buffer included in the image processing server or the receiving-side image converting apparatus.

(6)

The medical-use control system as recited in any of (2) to (5), including, in a case where the images are displayed on a plurality of the display apparatuses, a plurality of the receiving-side image converting apparatuses that output the images to the respective display apparatuses, in which the delay time control unit controls timings at which the images are output from the corresponding receiving-side image converting apparatuses, respectively, in accordance with the controlled delay times based on the frame rates of the individual display apparatuses.

(7)

The medical-use control system as recited in any of (2) to (6), in which in a case where the images are displayed on a plurality of the display apparatuses, the delay time control unit controls timings at which the images are output to all the display apparatuses, in accordance with a longest one of the controlled delay times based on the frame rates of the individual display apparatuses.

(8)

The medical-use control system as recited in any of (1) to (7), in which the delay time control unit acquires information of the medical device connected to the sending-side image converting apparatus, and sets the controlled delay time on the basis of a characteristic of the medical device.

(9)

The medical-use control system as recited in any of (1) to (8), in which with regard to one or more pieces of image processing performed in the image processing server, a time required for each piece of image processing is presented to a user with a graphical user interface (GUI).

(10)

The medical-use control system as recited in any of (1) to (9), in which the delay time control unit adjusts the controlled delay time in accordance with processing of an application executed by the image processing server or the receiving-side image converting apparatus.

(11)

The medical-use control system as recited in any of (1) to (10), in which in a case where resynchronization processing of a frame rate is executed in the display apparatus, the delay time control unit resets the controlled delay time in accordance with the frame rate after the resynchronization.

(12)

An image processing server constituting a medical-use control system in conjunction with:

a sending-side image converting apparatus configured to convert an image captured by a medical device into a transmission image to be transmitted via a network, and to send the image to the network; and a receiving-side image converting apparatus configured to receive the transmission image and the image generated by the image processing via the network, to convert the transmission image and the image generated by the image processing into display images, and to output the display images to a display apparatus, the image processing server including a delay time control unit configured to perform image processing on the image sent from the sending-side image converting apparatus via the network and to send the image generated by the image processing to the network, the delay time control unit being configured to obtain a controlled delay time based on a difference between a delay time in a first transmission path without via the image processing server and a delay time in a second transmission path via the image processing server, on the basis of a characteristic of the display apparatus, and to control a timing at which the images are output to the display apparatus.

(13)

A receiving-side image converting apparatus constituting a medical-use control system in conjunction with:

a sending-side image converting apparatus configured to convert an image captured by a medical device into a transmission image to be transmitted via a network, and to send the image to the network; and an image processing server configured to perform image processing on the image sent from the sending-side image converting apparatus via the network and to send an image generated by the image processing to the network, the image converting apparatus including a delay time control unit configured to receive the transmission image and the image generated by the image processing via the network, to convert the transmission image and the image generated by the image processing into display images, and to output the display images to a display apparatus, the delay time control unit being configured to obtain a controlled delay time based on a difference between a delay time in a first transmission path without via the image processing server and a delay time in a second transmission path via the image processing server, on the basis of a characteristic of the display apparatus, and to control a timing at which the images are output to the display apparatus.

(14)

A control method including:

causing a medical-use control system including:

a sending-side image converting apparatus configured to convert an image captured by a medical device into a transmission image to be transmitted via a network, and to send the image to the network;

an image processing server configured to perform image processing on the image sent from the sending-side image converting apparatus via the network and to send an image generated by the image processing to the network; and a receiving-side image converting apparatus configured to receive the transmission image and the image generated by the image processing via the network, to convert the transmission image and the image generated by the image processing into display images, and to output the display images to a display apparatus, to obtain a controlled delay time based on a difference between a delay time in a first transmission path without via the image processing server and a delay time in a second transmission path via the image processing server, on the basis of a characteristic of the display apparatus, and to control a timing at which the images are output to the display apparatus.

Note that the present embodiments are not limited to the foregoing embodiments, and various variations can be made within a range not departing from the gist of the present disclosure. Furthermore, the effects described in the present specification are merely exemplary and not limitative, and there may be achieved other effects.

REFERENCE SIGNS LIST

11 Medical-use image transmission system
21 Medical imaging apparatus
22 Sending apparatus
23 IP Switch
24 Image processing server
25 Receiving apparatus
26 Image receiving apparatus
31 IP Converter
32 Interface
33 Encoder 41 IP Converter
42 Decoder
43 Interface
51 IP Converter
52 Decoder
53 Frame buffer
54 Image processing unit
55 Frame buffer
56 Encoder
61 Delay time control apparatus
62 Delay execution unit
71 Frame rate acquisition unit
72 Delay time estimation unit
73 Controlled delay time calculation unit
74 Controlled delay time setting unit

The invention claimed is:

1. A medical-use control system comprising:
a sending-side image converting apparatus configured to convert an image captured by a medical device into a transmission image to be transmitted via a network, and to send the image to the network;
an image processing server configured to perform image processing on the image sent from the sending-side image converting apparatus via the network and to send an image generated by the image processing to the network;
a receiving-side image converting apparatus configured to receive the transmission image and the image generated by the image processing via the network, to convert the transmission image and the image generated by the image processing into display images, and to output the display images to a display apparatus; and
a delay time control unit configured to obtain a controlled delay time based on a difference between a delay time in a first transmission path without via the image processing server and a delay time in a second transmission path via the image processing server, on a basis of a characteristic of the display apparatus, and to control a timing at which the images are output to the display apparatus.

2. The medical-use control system according to claim 1, wherein
the delay time control unit obtains the controlled delay time by acquiring a frame rate of the display apparatus as the characteristic, and sets the controlled delay time for a delay execution unit provided on the second transmission path.

3. The medical-use control system according to claim 2, wherein
the delay time control unit obtains the controlled delay time that is an integral multiple of a reciprocal of the frame rate of the display apparatus.

4. The medical-use control system according to claim 3, wherein
the delay time control unit calculates the controlled delay time by determining an integer such that the controlled delay time becomes equal to or more than an image processing delay time estimated from one or more pieces of image processing set to be executed in the image processing server.

5. The medical-use control system according to claim 2, wherein
the delay execution unit comprises a frame buffer included in the image processing server or the receiving-side image converting apparatus.

6. The medical-use control system according to claim 2, comprising,
in a case where the images are displayed on a plurality of the display apparatuses, a plurality of the receiving-side image converting apparatuses that output the images to the respective display apparatuses,
wherein
the delay time control unit controls timings at which the images are output from the corresponding receiving-side image converting apparatuses, respectively, in accordance with the controlled delay times based on the frame rates of the individual display apparatuses.

7. The medical-use control system according to claim 2, wherein
in a case where the images are displayed on a plurality of the display apparatuses, the delay time control unit controls timings at which the images are output to all the display apparatuses, in accordance with a longest one of the controlled delay times based on the frame rates of the individual display apparatuses.

8. The medical-use control system according to claim 1, wherein
the delay time control unit acquires information of the medical device connected to the sending-side image converting apparatus, and sets the controlled delay time on a basis of a characteristic of the medical device.

9. The medical-use control system according to claim 1, wherein
with regard to one or more pieces of image processing performed in the image processing server, a time required for each piece of image processing is presented to a user with a graphical user interface (GUI).

10. The medical-use control system according to claim 1, wherein
the delay time control unit adjusts the controlled delay time in accordance with processing of an application executed by the image processing server or the receiving-side image converting apparatus.

11. The medical-use control system according to claim 1, wherein
in a case where resynchronization processing of a frame rate is executed in the display apparatus, the delay time control unit resets the controlled delay time in accordance with the frame rate after the resynchronization.

12. An image processing server constituting a medical-use control system in conjunction with:
a sending-side image converting apparatus configured to convert an image captured by a medical device into a transmission image to be transmitted via a network, and to send the image to the network; and
a receiving-side image converting apparatus configured to receive the transmission image and the image generated by the image processing via the network, to convert the transmission image and the image generated by the image processing into display images, and to output the display images to a display apparatus,
the image processing server comprising
a delay time control unit configured to perform image processing on the image sent from the sending-side image converting apparatus via the network and to send the image generated by the image processing to the network,
the delay time control unit being configured to obtain a controlled delay time based on a difference between a delay time in a first transmission path without via the image processing server and a delay time in a second transmission path via the image processing server, on a basis of a characteristic of the display apparatus, and to control a timing at which the images are output to the display apparatus.

13. A receiving-side image converting apparatus constituting a medical-use control system in conjunction with:
a sending-side image converting apparatus configured to convert an image captured by a medical device into a transmission image to be transmitted via a network, and to send the image to the network; and
an image processing server configured to perform image processing on the image sent from the sending-side image converting apparatus via the network and to send an image generated by the image processing to the network,
the image converting apparatus comprising
a delay time control unit configured to receive the transmission image and the image generated by the image processing via the network, to convert the transmission image and the image generated by the image processing into display images, and to output the display images to a display apparatus,
the delay time control unit being configured to obtain a controlled delay time based on a difference between a delay time in a first transmission path without via the image processing server and a delay time in a second transmission path via the image processing server, on a basis of a characteristic of the display apparatus, and to control a timing at which the images are output to the display apparatus.

14. A control method comprising:
causing a medical-use control system including:
a sending-side image converting apparatus configured to convert an image captured by a medical device into a transmission image to be transmitted via a network, and to send the image to the network;
an image processing server configured to perform image processing on the image sent from the sending-side image converting apparatus via the network and to send an image generated by the image processing to the network; and
a receiving-side image converting apparatus configured to receive the transmission image and the image generated by the image processing via the network, to convert the transmission image and the image generated by the image processing into display images, and to output the display images to a display apparatus,
to obtain a controlled delay time based on a difference between a delay time in a first transmission path without via the image processing server and a delay time in a second transmission path via the image processing server, on a basis of a characteristic of the display apparatus, and to control a timing at which the images are output to the display apparatus.

* * * * *